US006312466B1

(12) United States Patent
Robinson, Jr. et al.

(10) Patent No.: US 6,312,466 B1
(45) Date of Patent: Nov. 6, 2001

(54) PROSTHESIS CONTAINING A SOLUTION OF POLYETHYLENE GLYCOL

(75) Inventors: Jack B. Robinson, Jr., Duncanville; Rod J. Rohrich, Dallas, both of TX (US); Ronald M. Friedman, Loma Linda, CA (US)

(73) Assignee: Board of Regents, University of Texas System, Austin, TX (US)

( * ) Notice: Subject to any disclaimer, the term of this patent is extended or adjusted under 35 U.S.C. 154(b) by 0 days.

(21) Appl. No.: 08/447,217

(22) Filed: May 22, 1995

(51) Int. Cl.[7] ....................................................... A61F 2/02
(52) U.S. Cl. ................................. 623/11.11; 623/7; 623/8
(58) Field of Search ............................. 623/8, 11, 11.11, 623/7

(56) References Cited

U.S. PATENT DOCUMENTS

| | | | |
|---|---|---|---|
| 4,138,382 | 2/1979 | Polmanteer | 260/29.6 |
| 4,143,428 * | 3/1979 | Cohen | 623/8 |
| 4,157,085 * | 6/1979 | Austad | 623/8 |
| 4,404,296 * | 9/1983 | Schapel | 623/7 |
| 4,455,691 * | 6/1984 | Van Aken Redinger et al. | 623/8 |
| 4,495,509 * | 1/1985 | Chao | 346/215 |
| 4,713,073 * | 12/1987 | Reinmuller | 623/8 |
| 4,741,324 * | 5/1988 | Ina et al. | 126/263 |
| 5,067,965 | 11/1991 | Ersek et al. | 623/66 |
| 5,116,317 * | 5/1992 | Christensen et al. | 623/8 |
| 5,206,219 * | 4/1993 | Desai | 514/3 |
| 5,219,360 | 6/1993 | Georgiade | 623/8 |
| 5,246,454 * | 9/1993 | Peterson | 623/8 |
| 5,282,857 | 2/1994 | Perry et al. | 623/8 |
| 5,407,445 * | 4/1995 | Tautvydas et al. | 623/8 |
| 5,411,554 * | 5/1995 | Scopelianos et al. | 623/8 |
| 5,632,774 * | 5/1997 | Bobian | 623/8 |

OTHER PUBLICATIONS

Hawley's Condensed Chemical Dictionary, 11th Edition, (1987), p. 936, 1987.*

* cited by examiner

Primary Examiner—Paul B. Prebilic
(74) Attorney, Agent, or Firm—Fulbright & Jaworski

(57) ABSTRACT

There is disclosed medical prostheses filled with an aqueous solution of polyethylene glycol. The aqueous solution can be a saline solution. There is also disclosed a method of making such medical prostheses. The novel prostheses are useful, for example, as breast implants.

23 Claims, No Drawings

PROSTHESIS CONTAINING A SOLUTION OF POLYETHYLENE GLYCOL

BACKGROUND OF THE INVENTION

This invention relates to medical prostheses, particularly those medical prostheses used for a breast or testicular prosthesis.

Silicone-gel implants have fallen into disfavor in recent years which has created a need for new implants that can be used as medical prostheses. Medical prostheses from a safety standpoint should be chemically inert, noninflammatory, nonallergenic, and noncarcinogenic. In the case of breast implants, they ideally should also simulate the viscoelastic properties of the normal human breast, and be radiolucent to mammography. It is further important that breast implants create a natural "feel" and desirable aesthetics.

Much research has been directed toward finding alternative prostheses fitting this description. Although saline filled prostheses in large measure meet the criteria outlined above, saline prostheses create an unnatural feel and less than optical aesthetics. When implanted, for example, they tend to result in wrinkling of the overlying skin. In addition, Ersek et al. in U.S. Pat. No. 5,067,965 disclosed in column 1 that a prosthesis filled with saline alone undergoes accelerated breakdown of the outer shell of the prosthesis due to friction of the inner shell rubbing against itself. Due to this accelerated breakdown, the implants must be surgically replaced periodically, typically on the order of every four to five years. Ersek et al. further state that saline is a poor lubricating agent. Because of the relatively high amount of motion of the saline in the implant, the implant is also prone to fold-crease failure resulting in a rupture of the implant.

There is also a continuing need for implants that are radiolucent. It is therefore desirable that breast prostheses not unduly interfere with the ability to perform X-ray mammograms. Breast protheses that are radiographically dense can be serious impediments to effective mammography.

In addition, implants filled with saline alone may oftentimes not be usable for breast cancer patients who have undergone radiation therapy. Since the radiation weakens the tissue, the movement of the saline in the implant may be very painful to the patient such that the saline filled implant is not used.

SUMMARY OF THE INVENTION

The present invention concerns prostheses which address one or more of the problems described above.

In one broad respect, the present invention is a prosthesis useful for implantation into soft tissue, comprising an envelope that forms a hollow sealed shell defining an enclosed volume, wherein the enclosed volume of the hollow shell contains an aqueous solution of polyethylene glycol. In another broad respect, the present invention comprises a sealed, compliant envelope or capsule which is filled with an aqueous solution of polyethylene glycol.

Preferably, the polyethylene glycol will have a molecular weight of about 6,000 to about 20,000, and the viscosity of the aqueous solution will be from about 300 centistokes to about 450 centistokes, and the polyethylene glycol will preferably be present in the aqueous solution in an amount of from about 50 to about 85 weight/volume percent.

In a second broad respect, this invention is a method of making an implantable prosthesis, comprising filling an elastomeric envelope that forms a hollow sealed shell defining an enclosed volume with an aqueous solution of polyethylene glycol. In another broad respect, this invention is directed to a method of making an implantable prosthesis which comprises filling an elastomeric envelope with an aqueous solution of polyethylene glycol, and sealing the envelope to define an enclosed volume.

The envelope may be made of any of a number of elastomers which are employed in medical implants. The envelope may also be configured or otherwise shaped to conform to the shape of a body-organ or part upon being filled with a fluid or gel or the invention. It is important that the envelope be of a medical grade—i.e., that it be biocompatible, non-allergenic, noncarcinogenic and so forth. Particularly suitable envelopes or shells are fabricated from silicone elastomers and are available from McGhan Medical Corporation and other suppliers.

The prosthesis of this invention provides an implant that alleviates one or more of the problems discussed above. The present prosthesis employs a mixture of a saline solution and polyethylene glycol which possesses increased viscosity relative to saline alone. Advantageously, the saline/PEG blends of the present invention provide implants with a viscosity which enable the implants to possess characteristics simulating those of the body parts which they supplant. In general, saline solutions at best by themselves have viscosities which are too low for this purpose. Accordingly, the relative volumes and viscosities of the PEG components of the saline/PEG blends are selected to produce blends which possess the desired viscosities. Thus a saline/PEG blend having a viscosity of about 350 centistokes (cs) has been found to provide an implant which closely approaches the compliance and feel of breast tissue. The saline component alone had a viscosity of about 40 cs.

The prostheses of this invention that not only approximate the feel of human breast tissue, but the polyethylene glycol employed in the prostheses is considered to be a nontoxic, nonimmunogenic, and noncarcinogenic material. In that regard, PEG is routinely used in products ranging from cosmetics and food additives to bowel prep solutions. The prostheses of this invention, accordingly, are useful as an implant to augment or reconstruct human tissue, especially breast tissue.

DETAILED DESCRIPTION OF THE PREFERRED EMBODIMENTS

Polyethylene glycol is a well known material which can be made by well known procedures. Polyethylene glycol is also currently readily available commercially. The polyethylene glycol used in the practice of this invention is preferably of high purity and preferably free of impurities harmful to humans. Medical grade polyethylene glycol is therefore preferably employed. If needed, polyethylene glycol can be purified by a variety of well known techniques such as distillation, washing, and chromatography. Generally, the polyethylene glycols used in the practice of this invention are solids at room temperature. Polyethylene glycol used in the practice of this invention preferably has an average molecular weight of greater than 6,000, more preferably greater than 15,000, and most preferably greater than 20,000; preferably less than 50,000, more preferably less than 40,000, and most preferably less than 35,000.

The aqueous solutions containing polyethylene glycol used in the practice of this invention have a viscosity such that the resulting prosthesis exhibits a feel approximating human tissue. Generally the aqueous solution containing polyethylene glycol has a viscosity of greater than 300 centistokes, preferably greater than 350 centistokes; generally less than 450 centistokes, and preferably less than 400 centistokes. These viscosities can be measured using, for example, a cup viscometer.

While distilled water, for example, can be used to prepare the aqueous solution of polyethylene glycol, it is preferred in the practice of this invention to employ a saline solution. As is well known to those skilled in the art, saline is a 0.9 weight/volume percent sodium chloride solution (0.9 grams of NaCl in 100 cubic centimeters of water). It should be appreciated that the concentration of sodium chloride can be varied, however. The aqueous solutions containing polyethylene glycol are generally prepared by weighing out the desired amount of polyethylene glycol, adding up to the desired volume of water or saline and heating gently (e.g., 55–65 degrees C.) until the polyethylene glycol is dissolved. While the polyethylene glycol can be dissolved at room temperature with stirring, this procedure is less preferred since the polyethylene glycol readily dissolves at the elevated temperature.

As stated earlier, the envelope used in the practice of this invention can be made from materials used in preparing medical prostheses such as breast implants. Representative examples of materials used for the envelopes include polyurethanes and silicone elastomers. Owing to the current restrictions made by governmental agencies, particularly preferred envelopes are made of vulcanized silicone rubber. The preferred envelopes used in the practice of this invention are double lumen, which are composed of a water impermeable inner shell, typically made of Teflon™ tetrafluoroethylene fluorocarbon polymers. The envelopes used in the practice of this invention are readily available commercially, typically configured with an orifice for receipt of the filler material, such as a fill valve having an internal valve to prevent backflow and a plug which can be additionally sealed by inserting the plug to fill the orifice. Such envelopes are made by well known techniques and are currently available commercially from sources such as Dow Corning Corporation and McGhan Medical Corporation. Preferably the envelope is a silicone elastomer prosthetic shell. The envelope can also contain an orifice so that the prosthesis can be filled with the aqueous solution of polyethylene glycol after the envelope is implanted.

As stated earlier, mixtures of saline and polyethylene glycol is employed to fill the envelope, the mixtures having viscosities enabling the prostheses to simulate the compliance and other physical characteristics of the human tissues they effectively replace. In that regard, the mixture preferably contains greater than 50 weight/volume percent of polyethylene glycol, more preferably greater than 60 weight/volume percent of polyethylene glycol; preferably less than 85 weight/volume percent polyethylene glycol. The most preferred aqueous solution contains about 80 to about 85 weight/volume percent polyethylene glycol.

If desired, additional additives can be included along with the polyethylene glycol contained in the envelope, such as, for example, antioxidants, lubricating agents such as ethylene glycol, propylene glycol, butanetriol, hexanediol, hexanetriol, glycerol, glyceride, and triglyceride, pH controlling agents such as sodium hydroxide, antibacterial agents, and preservatives. The envelope is then sealed using well known techniques to seal the envelope thereby forming the final prosthesis.

The prostheses of this invention are prepared by filling an envelope described above with an aqueous solution of polyethylene glycol. The envelope can be filled by loading a sterile syringe with the aqueous solution of polyethylene glycol and injecting the solution either manually or by a syringe pumping machine into the implants until the required volume is placed inside the implant. Since the solution is less viscous at elevated temperatures, it may be desirable, depending on the viscosity of the solution, the size of the needle and so forth, to inject warm solution to more easily inject the solution.

The prosthesis of this invention can be used to replace or augment human tissue. The process for using the prosthesis involves placing the prosthesis submuscularly in a human being in a region where replacement or augmentation is desired. For example, for breast augmentation the prosthesis is subcutaneously placed into the breast region. The process for placing the prosthesis into a human is known to those skilled in the art using surgical procedures, generally involving inserting the implant through an incision in the body.

The following examples are provided to illustrate the invention and are not to be construed as limiting the scope of the claims or the invention.

Eighteen rabbits underwent dorsal subfascial implantation of 25 ml silicone elastomer prosthetic shells (McGhan Medical Corp.) inflated with an 85% weight/volume solution of polyethylene glycol/saline having an average molecular weight of 20,000. The aqueous saline solution of polyethylene glycol was prepared by weighing out the appropriate amount of polyethylene glycol, adding up to volume saline and heating gently at 55 to 65 degrees C. until the polyethylene glycol was dissolved. Next, the solution was loaded into a sterile syringe and either manually or driven by a syringe pumping machine into the implants until the required volume was placed inside the implant. Four control animals were implanted with saline prostheses of equal volume. All animals were anesthetized with ketamine (50 mg/kg) and xylazine (10 mg/kg) intramuscularly and given penicillin G (20,000 u/kg) preoperatively. After two weeks of wound healing, some of the implants were subjected to catastrophic failure by repeated puncture with a 14 gauge needle. Rupture was confirmed by aspiration of the implant contents. The animals were closely monitored for potential signs of toxicity, including anorexia, behavioral changes, and systemic illness. The rabbits were sacrificed at intervals of 6 weeks and 8 months. The prosthetic capsule, spleen, liver, kidneys, and locoregional lymph nodes were examined for histopathologic changes, using hematoxylin and eosin staining.

Polyethylene glycol/saline implant viscosity was analyzed by measuring flow velocity in a cup viscometer. Compliance of several types of prostheses, as well as normal breast tissue, was determined by dropping a 10 gram weight on each from a height of 20 cm. The amplitude and duration of vibrations produced at the implant or breast surface was measured by a sensor composed of a steel pin touching the vibrating surface, the pin attached to a permanent magnet housed inside a sleeve wrapped in 50 turns of copper wire. The induced voltage in the wire caused by the movement of the magnet was measured and displayed on an oscilloscope.

Mammography of a variety of breast implant materials was performed, using a standard phantom (American College of Radiology) to simulate breast calcifications and soft tissue masses. Images were recorded at 28 kV with a tube-to-film distance of 55 cm and autotimer control of exposure, as described by Gumico et al., *Plast. Reconstr. Surg.*, 84:772 (1989).

No evidence of toxicity was noted among rabbits implanted with the polyethylene glycol/saline prostheses.

One animal died shortly after implant placement due to an unrelated respiratory illness. Twelve polyethylene glycol/saline rabbits were sacrificed 8 weeks postoperatively, while 5 animals were sacrificed at 6 months. Histologic examination demonstrated no implant material and no pathologic changes in the spleen, liver, kidneys, and locoregional lymph nodes. The prosthetic capsule was also free of polyethylene glycol and showed no foreign body response. Polyethylene glycol/saline viscosity was 350 centistokes as measured using a cup viscometer, as compared to 40 cs for saline. A motion detector and a standard applied force were used to determine quantitatively the motion obtained in the various types of implants tested as an indicator of tactile properties. Saline implants demonstrated large oscillation amplitudes (>22 millivolts) and durations (>1.1 seconds). In contrast, low amplitudes (<16 millivolts) and durations (<0.7 seconds) were observed with displacement of human breast tissue, silicone-gel implants and polyethylene glycol/saline.

On mammographic examination, the polyethylene glycol/saline implants demonstrated radiolucency comparable to saline and superior to silicone-gel. Polyethylene glycol/saline did not appear to significantly inhibit mamrnmographic interpretation.

In addition, a number of breast implants were prepared using the procedure outlined above. Thus, breast implants were made using polyethylene glycol having a molecular weight of 200 (no saline addition: polyethylene glycol being a liquid at room temperature when less than a molecular weight of about 800) through 20,000 at 70% weight/volume. Solutions have also been made with polyethylene glycol having a molecular weight of up to 100,000. In addition, these implants were qualitatively compared as to feel against saline and silicone implants, with the best results shown for the implants of this invention containing polyethylene having a molecular weight of 8000 in a 50% weight/volume solution through implants containing polyethylene having a molecular weight of 20,000 in a 70% weight/volume solution.

What is claimed is:

1. A prosthesis useful for implantation into soft tissue, comprising an envelope that forms a hollow sealed water impermeable shell defining an enclosed volume, wherein the enclosed volume of the hollow shell contains an aqueous solution of polyethylene glycol.

2. The prosthesis of claim 1, wherein the envelope is made of vulcanized silicone rubber.

3. The prosthesis of claim 1, wherein the polyethylene glycol has a molecular weight of about 6000 to about 20000.

4. The prosthesis of claim 1, wherein the aqueous solution is a saline solution.

5. The prosthesis of claim 1, wherein the viscosity of the aqueous solution is from about 300 centistokes to about 450 centistokes.

6. The prosthesis of claim 1, wherein the polyethylene glycol is present in the aqueous solution in an amount from about 50 to about 85 weight/volume percent.

7. The prosthesis of claim 1, wherein the polyethylene glycol has a molecular weight of about 20,000.

8. The prosthesis of claim 1, wherein the envelope is made of vulcanized silicone rubber, wherein the polyethylene glycol has a molecular weight of about 6000 to about 20000, wherein the aqueous solution is a saline solution, wherein the viscosity of the aqueous solution is from about 300 centistokes to about 450 centistokes and wherein the polyethylene glycol is present in the aqueous solution in an amount from about 50 to about 85 weight/volume percent.

9. A prosthesis comprising a sealed compliant water impermeable envelope or capsule which is filled with an aqueous solution of polyethylene glycol.

10. The prosthesis of claim 9, wherein the envelope is made of vulcanized silicone rubber.

11. The prosthesis of claim 9, wherein the polyethylene glycol has a molecular weight of about 6000 to about 20000.

12. The prosthesis of claim 9, wherein the aqueous solution is a saline solution.

13. The prosthesis of claim 9, wherein the viscosity of the aqueous solution is from about 300 centistokes to about 450 centistokes.

14. The prosthesis of claim 9, wherein the polyethylene glycol is present in the aqueous solution in an amount from about 50 to about 85 weight/volume percent.

15. The prosthesis of claim 9, wherein the prosthesis is adapted for use as a breast implant, wherein the envelope is made of vulcanized silicone rubber, wherein the polyethylene glycol has a molecular weight of about 6000 to about 20000, wherein the aqueous solution is a saline solution, wherein the viscosity of the aqueous solution is from about 300 centistokes to about 450 centistokes and wherein the polyethylene glycol is present in the aqueous solution in an amount from about 50 to about 85 weight/volume percent.

16. A method of making an implantable prosthesis, comprising filling an elastomeric water impermeable envelope that forms a hollow shell defining an enclosed volume with an aqueous solution of polyethylene glycol and then sealing the envelope.

17. The method of claim 16, wherein the envelope is made of vulcanized silicone rubber.

18. The method of claim 16, wherein the polyethylene glycol has a molecular weight of about 6000 to about 20000 and wherein the viscosity of the aqueous solution is from about 300 centistokes to about 450 centistokes.

19. The method of claim 16, wherein the aqueous solution is a saline solution containing polyethylene glycol in the aqueous solution in an amount from about 50 to about 85 weight/volume percent.

20. The method of claim 16, wherein the envelope is filled by injecting the aqueous solution into the envelope using a syringe loaded with the aqueous solution.

21. The prosthesis of claim 1, wherein the envelope comprises a double lumen.

22. The prosthesis of claim 9, wherein the envelope comprises a double lumen.

23. The method of claim 16, wherein the envelope comprises a double lumen.

* * * * *